(12) United States Patent
Yamamoto (10) Patent No.: US 11,980,365 B2
(45) Date of Patent: May 14, 2024

(54) SURGICAL CLIP (71) Applicant: CHARMANT INC., Sabae (JP)

(72) Inventor: Katsumi Yamamoto, Sabae (JP)

(73) Assignee: CHARMANT INC., Sabae (JP)

( * ) Notice: Subject to any disclaimer, the term of this patent is extended or adjusted under 35 U.S.C. 154(b) by 897 days.

(21) Appl. No.: 17/044,046

(22) PCT Filed: Jul. 23, 2020

(86) PCT No.: PCT/JP2020/028589
§ 371 (c)(1),
(2) Date: Sep. 30, 2020

(87) PCT Pub. No.: WO2021/124606
PCT Pub. Date: Jun. 24, 2021

(65) Prior Publication Data
US 2021/0236127 A1 Aug. 5, 2021

(30) Foreign Application Priority Data
Dec. 15, 2019 (JP) ................. 2019-226026

(51) Int. Cl.
A61B 17/08 (2006.01)
A61B 17/10 (2006.01)
(Continued)

(52) U.S. Cl.
CPC ............ A61B 17/083 (2013.01); A61B 17/10 (2013.01); A61B 2017/081 (2013.01); A61B 17/29 (2013.01); A61B 2034/302 (2016.02)

(58) Field of Classification Search
CPC ... A61B 17/083; A61B 17/10; A61B 17/1227; A61B 17/128
See application file for complete search history.

(56) References Cited

U.S. PATENT DOCUMENTS 6,210,418 B1 4/2001 Storz et al.
9,289,216 B2 3/2016 Weisshaupt et al.
(Continued)

FOREIGN PATENT DOCUMENTS

CN 102125452 A 7/2011
JP H10-503390 A 3/1998
(Continued)

OTHER PUBLICATIONS

PCT/ISA/210, "International Search Report for International Application No. PCT/JP2020/028589," Oct. 6, 2020.

Primary Examiner — Christine H Matthews
(74) Attorney, Agent, or Firm — HAUPTMAN HAM, LLP (57) ABSTRACT To provide a surgical clip capable of being held by, in particular, a robot arm or other device, thus promoting automation of a procedure. A surgical clip to pull an organ or other body tissue so as to provide an area necessary for an operation includes: a pair of upper and lower holders to hold the organ or other body tissue therebetween; a grip to open and close the holders; an urger to constantly urge the holders in a holding direction; and an engagement portion provided on the grip. The engagement portion comes into engagement with a hole defined in a functional part provided on a medical device that includes any one of a robot, forceps, and an applier. The functional part is configured to open and close so as to perform a holding, incising, or other operation.

5 Claims, 4 Drawing Sheets (51) Int. Cl.
   *A61B 17/29* (2006.01)
   *A61B 34/30* (2016.01)

(56) References Cited

U.S. PATENT DOCUMENTS

| | | |
|---|---|---|
| 10,716,546 B2 | 7/2020 | Adkisson et al. |
| 2009/0192527 A1 | 7/2009 | Messas |
| 2012/0184976 A1 | 7/2012 | Nakamura |
| 2013/0184726 A1* | 7/2013 | Weisshaupt ........ A61B 17/1227 |
| | | 606/158 |

FOREIGN PATENT DOCUMENTS

| | | |
|---|---|---|
| JP | 3157486 U | 2/2010 |
| JP | 2013-537052 A | 9/2013 |
| JP | 2018-528006 A | 9/2018 |
| JP | 6546921 B2 | 7/2019 |
| WO | 01/58367 A1 | 8/2001 |

* cited by examiner

SURGICAL CLIP

RELATED APPLICATIONS

The present application is National Phase of International Application No. PCT/JP2020/028589 filed Jul. 23, 2020, and claims priority from Japanese Application No. 2019-226026, filed Dec. 15, 2019, the disclosure of which is hereby incorporated by reference herein in its entirety.

TECHNICAL FIELD

The present invention relates to a surgical clip that provides an area necessary for an operation by pulling an organ or other body tissue during surgery and that is also usable as forceps or a hemostatic clip. The present invention also relates to a surgical clip usable in common not only for a plurality of types of surgical robots manufactured by different manufacturers or in accordance with different specifications and having different forms, but also for other medical devices, such as forceps and appliers.

BACKGROUND ART

During surgery, an organ or other body tissue that is not targeted for an operation may become an obstacle, which may hinder the operation performed by a surgeon. A solution to such a problem involves pulling, with a surgical clip, the organ or body tissue hindering the operation, thus providing an area necessary for the operation (see, for example, Patent Literature 1).

In recent years, surgery assist systems using robots have found widespread use, with the aim of improving treatment results or increasing treatment application range. Particularly well-known examples of a thoracic or abdominal cavity endoscopic operation robot include a da Vinci® surgical system manufactured by Intuitive Surgical, Inc. in USA. A surgical operation performed using such a robot involves, for example, holding and pulling the organ or body tissue by a functional part on a movable arm tip, thus providing an area necessary for the operation (see, for example, Patent Literature 2).

CITATION LIST

Patent Literature

[Patent Literature 1] Japanese Unexamined Patent Application Publication (Translation of PCT Application) No. 2010-505504

[Patent Literature 2] Japanese Unexamined Patent Application Publication No. 2015-2922

SUMMARY OF THE INVENTION

Problem to be Solved by the Invention

Surgery that uses such a surgical robot involves using a tube called a "trocar", inserting the arm into the trocar, with the trocar placed in an abdominal cavity, and performing a certain procedure on the organ or body tissue with the functional part. Such conventional surgical robots described above have problems described below.

(i) A dedicated arm is necessary for each of robots manufactured by different manufacturers or in accordance with different specifications. This allows no compatibility.

(ii) A robot with three arms, for example, is only capable of holding the organ or body tissue from only three directions.

(iii) When the organ or other body tissue must be held from more than three directions, another robot has to be placed close to an operating table. This, however, limits the range in which a practitioner, such as a doctor or a nurse, can act, because the surrounding area of the operating table is occupied by the robots. In addition, a large number of arms will be in the way, which blocks the practitioner's view or causes a hindrance to the procedure.

(iv) In principle, only a single arm is insertable into a single trocar. This means that under the current circumstances, a single trocar is exclusively occupied by an arm for holding and pulling an organ or other body tissue.

(v) A dedicated arm is required for each of different affected areas, such as a stomach, a heart, a bladder, and a brain, making it necessary to replace the arm on an as-needed basis. Such dedicated arms, however, are not only expensive but also disposable from a hygienic standpoint, considerably increasing the cost of an operation to be performed using the surgical robot.

(vi) Using a plurality of arms for the purpose of holding the organ or body tissue causes the robot to run out of arms usable for different purposes, making it impossible to efficiently use expensive arms.

The present invention has been made to solve the problems (i) to (vi).

Means for Solving the Problem

The inventor of the present invention focused his attention on a hole in a holder on an arm tip used in many recent surgical robots. When an organ or other body tissue is held by a functional part on the arm tip, a portion of the organ or other body tissue enters the hole, so that the organ or other body tissue is held more securely. The inventor came to the conclusion that if a surgical clip is allowed to be gripped by the functional part on the arm of the surgical robot using the hole, the above-described problems are solvable, and thus came up with the idea of the present invention.

Specifically, the invention according to the first aspect provides a surgical clip (2) to pull an organ or other body tissue so as to provide an area necessary for an operation. The surgical clip (2) includes: a pair of upper and lower holders (21) to hold the organ or other body tissue therebetween; a grip (22) to open and close the holders; an urger to constantly urge the holders in a holding direction; and an engagement portion provided on the grip. The engagement portion comes into engagement with a hole defined in a functional part provided on a medical device that includes any one of a robot, forceps, and an applier. The functional part is configured to open and close so as to perform a holding, incising, or other operation.

Because the present invention is embodied as described above, bringing the engagement portion into engagement with the hole defined in the functional part and opening and closing the functional part make it possible to open and close the surgical clip so as to hold the organ or other body tissue. In particular, when the functional part is provided on an arm tip of a surgical robot, the organ or other body tissue is held and pulled by the surgical clip gripped by the functional part, and then another surgical clip is gripped by the functional part on the arm tip, thus making it possible to hold and pull another portion of the organ or other tissue.

As recited in the second aspect, the engagement portion may be formed into a cone including a frustum such that the engagement portion is capable of coming into engagement with the hole that varies in width, diameter, or shape. Thus, if the hole varies in width, diameter, or shape depending on manufacturers or specifications, the surgical clip would be usable in common. Forming the engagement portion into a cone facilitates engagement of the engagement portion with the hole. This makes it possible to perform the process of causing the functional part to grip the surgical clip easily in a short time.

As used herein, the term "cone" according to the present invention not only includes a circular cone and a pyramid, but also includes: frustums, such as a circular truncated cone obtained by cutting off the top of the circular cone and a truncated pyramid obtained by cutting off the top of the pyramid; and shapes obtained by forming the tops of such cones or pyramids into spherical shapes.

As recited in the third aspect, the engagement portion is preferably formed into a circular cone or a regular polygonal pyramid. Forming the engagement portion into a circular cone makes it possible to freely change the orientation of the surgical clip gripped by the functional part. Forming the engagement portion into a regular polygonal pyramid makes it possible to effect positioning of the surgical clip at a predetermined rotation angle position so as to fix the orientation of the surgical clip gripped by the functional part.

As recited in the fourth aspect, the engagement portion may be provided with an engagement groove capable of coming into engagement with a tooth or a projection provided on the functional part of the medical device.

Providing such an engagement groove in the engagement portion capable of coming into engagement with the hole in the functional part allows the surgical clip to be gripped by, for example, another functional part that does not include the hole but includes a tooth or a projection, and enables the surgical clip to hold the organ or other body tissue, resulting in a further increase in general versatility. As recited in the fifth aspect, providing the engagement portion with a plurality of the engagement grooves at different angles more easily allows the surgical clip to be gripped by the functional part including the tooth or projection, and enables fixation of the surgical clip at a certain rotation angle position.

In order to allow the functional part to grip the surgical clip so as to perform opening and closing operations when the functional part on the arm tip is opened and closed by a driver, such as a cylinder, a motor, a solenoid, or other driving means, the urging force of the urger needs to be smaller than the force by which the driver opens and closes the functional part as recited in the sixth aspect.

The force to be produced by the driver for the surgical robot in opening and closing the functional part is usually set to a necessary minimum so as not to damage the organ or other body tissue. Thus, the urger to constantly urge the holders of the surgical clip in the holding direction needs to allow the surgical clip to be opened and closed with such a small force. In order to strongly hold the organ or other body tissue using such an urger, the surgical clip preferably includes tooth rows (23) each provided on an associated one of the holders as recited in the seventh aspect. The tooth rows preferably each include teeth that bite into the organ or other body tissue. The teeth are preferably inclined toward a direction identical to a pulling direction. The tooth rows (23) on the upper and lower holders (21) are preferably deviated from each other such that the teeth are in mesh with each other in a staggered manner.

As recited in the eighth aspect, the hole may be formed into an elongated hole, and the engagement portion (24) may be movable in a longitudinal direction, with the engagement portion fitted into the hole. This makes it possible to not only allow the surgical clip to be gripped by the functional part such that the surgical clip is rotatable relative to the functional part but also allow the surgical clip to be gripped by the functional part such that the surgical clip is movable in the longitudinal direction.

As recited in the ninth aspect, an outer periphery of the engagement portion (24) may be provided with gear protrusion and indentation, and an engagement hole (1a) in the tip (1) of the robot hand or an inner surface of the engagement groove may be provided with a projection that comes into engagement with the protrusion and indentation, thus providing a ratchet mechanism so as to enable rotation angle positioning of the grip (22).

Effects of the Invention

If surgical robots are manufactured by different manufacturers or in accordance with different specifications, the present invention would allow a shared-use surgical clip to be gripped by functional parts so as to hold an organ or other body tissue. This enables the surgical clip to be shared between the surgical robots manufactured by different manufacturers or in accordance with different specifications, thus achieving general versatility.

The surgical clip according to the present invention assumes the role of holding and pulling the organ or other body tissue. Suppose that the surgical clip gripped by the functional part is moved to a predetermined position with an arm, the organ or other body tissue is held by the surgical clip at this position, and then the functional part ceases gripping the surgical clip. In this case, the arm will be usable for other purposes, enabling efficient use of a small number of arms. A trocar into which the surgical clip is inserted is insertable into an arm for a different purpose.

The manufacturing cost of the surgical clip is lower than those of arms. In addition, the efficient use of the arms enables a significant reduction in the cost of an operation that involves the use of a surgical robot.

BRIEF DESCRIPTION OF THE DRAWINGS

FIG. 7 is a partially enlarged plan view of the surgical clip and the functional part, illustrating other effects of grooves 24a.

BEST MODES FOR CARRYING OUT THE INVENTION

Preferred embodiments of surgical clips according to the present invention will be described in detail with reference to the drawings.

Figure 1A:
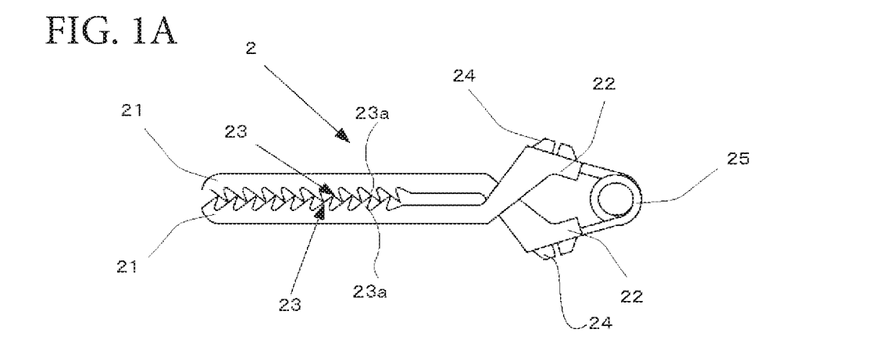
FIG. 1(a) is a side view of a surgical clip according to an embodiment of the present invention, with holders closed.
Figure 1B:
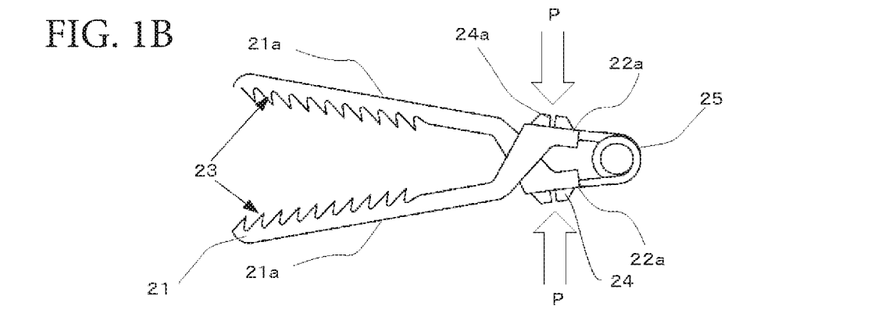
FIG. 1(b) is a side view of the surgical clip, with the holders opened.
Figure 1C:
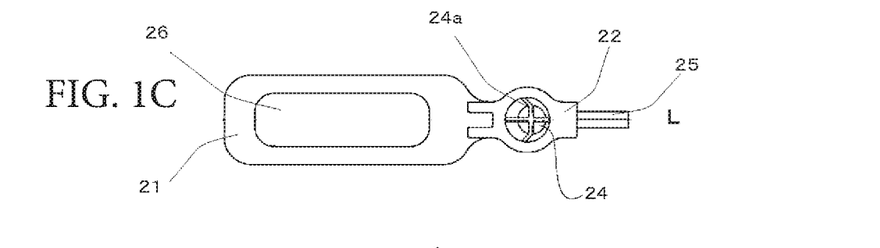
FIG. 1(c) is a plan view of the surgical clip.
Figure 1D:
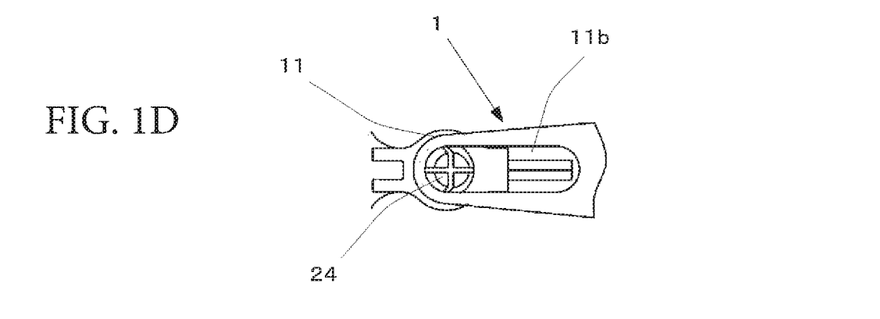
FIG. 1(d) is a partial plan view of an arm tip, illustrating engagement of engagement portions of the surgical clip with the inside of holes defined in a functional part on the arm tip of a medical device.
Figure 2:
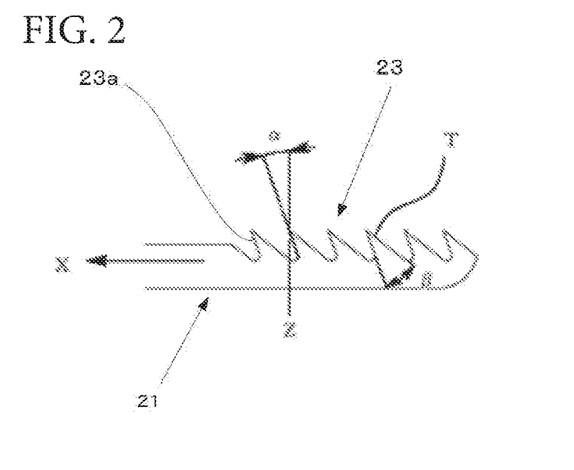
FIG. 2 is a partially enlarged side view of the surgical clip according to this embodiment, illustrating a tooth inclination angle and a tooth tip angle.
Figure 3:
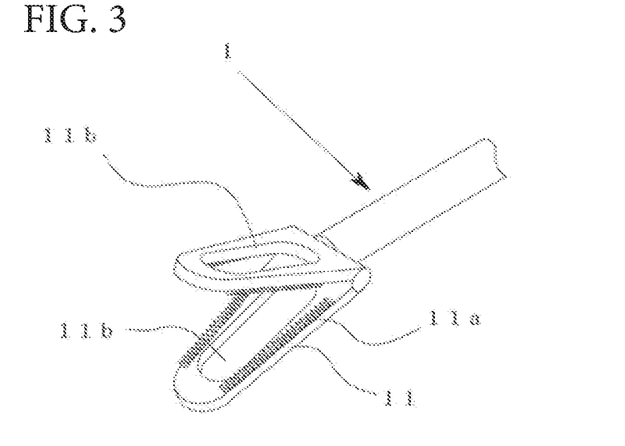
FIG. 3 is an enlarged perspective view of the functional part on the arm tip according to one example, illustrating the details of the functional part.

FIG. 1(a) is a side view of a surgical clip according to an embodiment of the present invention, with holders closed. FIG. 1(b) is a side view of the surgical clip, with the holders opened. FIG. 1(c) is a plan view of the surgical clip. FIG. 1(d) is a partial plan view of an arm tip, illustrating engagement of engagement portions of the surgical clip with the inside of holes defined in a functional part on the arm tip of a medical device. FIG. 2 is a partially enlarged side view of the surgical clip according to this embodiment, illustrating a tooth inclination angle and a tooth tip angle. FIG. 3 is an enlarged perspective view of the functional part according to one example, illustrating the details of the functional part.

A surgical clip 2 includes: a pair of upper and lower holders 21, 21 to hold an organ or other body tissue (which will hereinafter be referred to as an "organ or other tissue") therebetween; grips 22, 22 each integral with an associated one of the pair of holders 21, 21 and configured to open and close the holders 21, 21; tooth rows 23 each defined on an associated one of the holders 21, 21 and including teeth 23a arranged in a direction identical to a pulling direction; and a helical spring 25 connecting a pair of the upper and lower grips 22, 22 and serving as an urger to constantly urge the holders 21, 21 in a closing direction (i.e., a direction in which the organ or other tissue is to be held). The basic structure of the surgical clip 2 of this type is known in, for example, Japanese Patent No. 6546921 granted to the applicant of the present application.

The holders 21, 21 are provided in an intersecting manner such that the holders 21, 21 open upon receiving pressing forces P that act against the spring 25 from above and below the grips 22, 22. In the example illustrated, each of the tooth rows 23, provided on an associated one of the upper and lower holders 21, 21, includes two parallel rows, and an elongated hole 26 to allow the associated tooth row 23 to bite into the organ or other tissue is defined between the two rows included in the associated tooth row 23, such that the elongated holes 26 pass through the holders 21, 21. The organ or other tissue, which is relatively soft, enters the elongated holes 26, causing the tooth rows 23, 23 to bite into the organ or other tissue. The elongated holes 26 thus function in conjunction with the tooth rows 23, 23 so as to further increase the force by which the surgical clip 1 bites into the organ or other tissue. Through the elongated holes 26, a user is able to visually check the degree of biting of the tooth rows 23, 23 into the organ or other tissue.

As illustrated in FIG. 1(a), the teeth constituting the upper and lower tooth rows 23, 23 are disposed such that the upper teeth and the lower teeth are in mesh with each other in a staggered manner. As illustrated in FIG. 2, the teeth 23a constituting the tooth rows 23 are inclined toward a direction that blocks disengagement from the organ or other tissue, i.e., toward a direction identical to a direction X in which a pulling force is to be exerted.

Selecting suitable values for an inclination angle $\alpha$ (which is an angle of each tooth with respect to a normal direction Z perpendicular to the pulling direction X) and a tooth tip angle $\beta$ makes it possible to increase, with no damage done to the organ or other tissue, the biting force without changing the resilient force of the spring 25, the sizes of the teeth 23a, or the number of teeth 23a. Optimal values obtained by experiment in relation to pitches between the teeth 23a may be determined to be the suitable values for the inclination angle $\alpha$ and the tooth tip angle $\beta$ of each tooth 23a.

When each pitch between the teeth 23a is, for example, about 1.5 mm, the inclination angle $\alpha$ may be in the range of, for example, 17° to 19°, and the tooth tip angle $\beta$ may be in the range of, for example, 50° to 55°. Selecting suitable values for the inclination angle $\alpha$ and the tooth tip angle $\beta$ in relation to the pitches, adjusting the spring force of the spring 25, and using the staggered upper and lower tooth rows 23, 23 would enable the surgical clip 2 according to the present invention to produce a sufficiently high holding force if the surgical clip 2 is small in size. Accordingly, if a trocar has a small inner diameter, the surgical clip 2 whose size is reduced in accordance with the inner diameter would be prepared, so that the surgical clip 2 is insertable into the body of a patient using a body cavity insertion instrument.

In the example illustrated in FIG. 3, an openable and closable functional part 11 on a tip of an arm 1 is provided with teeth 11a by which the organ or other tissue is to be held. During procedure, a portion of the organ or other tissue, for example, is held and turned over by the functional part 11 so as to create a space that allows entry of a scalpel (or a functional part) on the tip of another arm 1. The functional part 11 thus functions in conjunction with the scalpel in, for example, cutting an affected area.

Figure 4A:
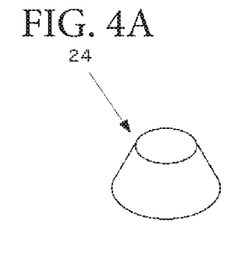
FIG. 4(a) is a diagram illustrating an example of the engagement portion in the form of a circular truncated cone obtained by cutting off the top of a circular cone.
Figure 4B:
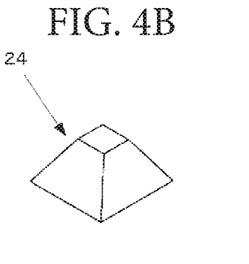
FIG. 4(b) is a diagram illustrating an example of the engagement portion in the form of a truncated square pyramid obtained by cutting off the top of a pyramid.
Figure 4C:
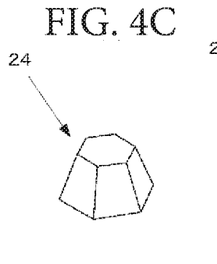
FIG. 4(c) is a diagram illustrating an example of the engagement portion in the form of a polygonal truncated pyramid.
Figure 4D:
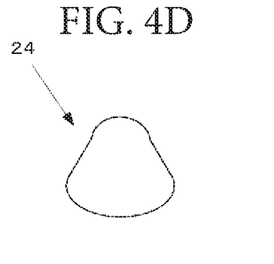
FIG. 4(d) is a diagram illustrating an example of the engagement portion obtained by forming the top of a circular truncated cone into a spherical shape.

The functional part 11 is provided with elongated holes 11b passing therethrough. The grips 22, 22 are provided with engagement portions 24, 24 that are able to come into engagement with the holes 11b. The engagement portions 24, 24 preferably each have a conical shape with a tapered peripheral surface such that the engagement portions 24, 24 are easily brought into engagement with the holes 11b and such that the engagement portions 24, 24 would be able to come into engagement with the holes 11b if the widths, diameters, or shapes of the holes 11b, for example, slightly vary depending on manufacturers or specifications. As illustrated in FIGS. 4(a)-4(d), the term "conical shape" not only includes a circular cone and a pyramid, but also includes: frustums, such as a circular truncated cone (see FIG. 4(a)) obtained by cutting off the top of the circular cone, a truncated square pyramid (see FIG. 4(b)) obtained by cutting off the top of the pyramid, and a polygonal truncated pyramid (see FIG. 4(c)); and shapes obtained by forming the tops of such cones or pyramids into spherical shapes (see FIG. 4(d)). The shape illustrated in FIG. 4(d) is obtained by forming the top of the circular cone illustrated in FIG. 4(a), for example, into a spherical shape. In this embodiment, the engagement portions 24, 24 are formed into circular truncated cones as illustrated in FIGS. 1(a)-1(d).

Figure 5:
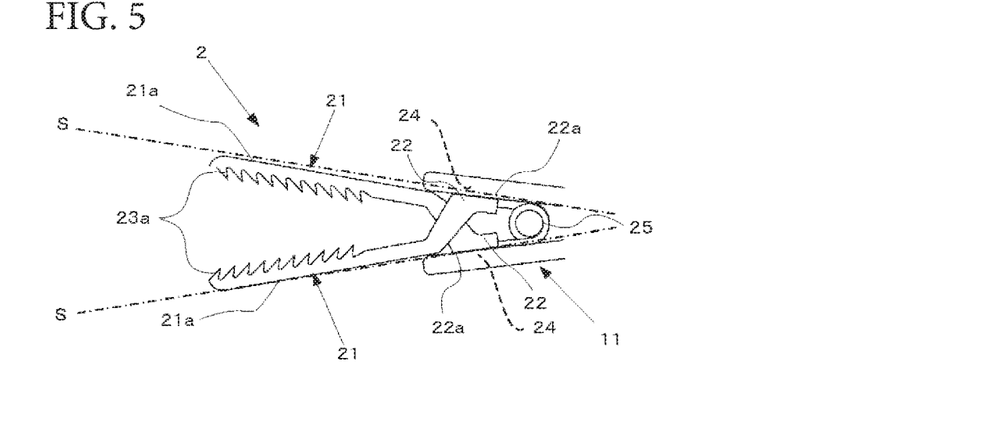
FIG. 5 is a diagram illustrating a state where each circular truncated conical engagement portion is fitted into and engaged with the associated hole in the functional part on the arm tip, and the surgical clip is thus gripped by the arm tip.

As illustrated in FIG. 5, each circular truncated conical engagement portion 24 is fitted into the associated hole 11b in the functional part 11. The surgical clip 2 is thus gripped by the tip of the arm 1. During this process, if the center of each hole 11b in the functional part 11 is slightly deviated from the center of the associated engagement portion 24, entry of the top of each engagement portion 24 into the associated hole 11b in the functional part 11 would cause the tapered peripheral surface to effect positioning of each engagement portion 24 with respect to the associated hole 11b. This easily enables the surgical clip 2 to be gripped by the tip of the arm 1. With the surgical clip 2 gripped, the functional part 11 is operated in a closing direction. This opens the holders 21 of the surgical clip 2, thus enabling the organ or other tissue to be held by the holders 21.

The coil diameter of the spring 25 serving as the urger is small enough to prevent the spring 25 from interfering with the functional part 11 when the surgical clip 2 is gripped by the tip of the arm 1. The urging force of the spring 25 allows the functional part 11 to open and close in accordance with opening and closing operations of the functional part 11. The functional part 11 is often opened and closed by a driver, such as a cylinder, a motor, or a solenoid. The urging force of the spring 25 is smaller than a driving force produced when the functional part 11 is closed by the driver. If the spring 25 has a diameter and an urging force that satisfy the conditions just mentioned, suitable values are selected for the arrangement, the inclination angle α, and the tooth tip angle β (see FIG. 2) of the teeth 23a of the holders 21 as previously described, such that the organ or other tissue is held and pulled with great force.

As illustrated in FIG. 5, a surface 21a of each holder 21 is preferably located within substantially the same plane as a surface 22a of the associated grip 22 (i.e., within an associated one of planes indicated by the alternate long and short dashed lines S in FIG. 5) or located inward of the associated plane S, such that the functional part 11 and the holders 21 will not interfere with each other when the functional part 11 is closed and the holders 21 of the surgical clip 2 are opened.

Figure 6:
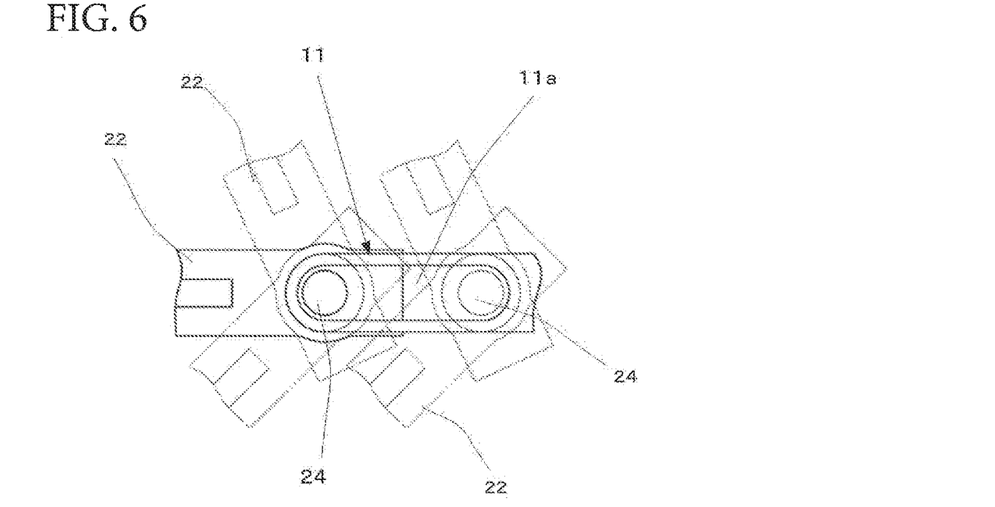
FIG. 6 is a partially enlarged plan view of the surgical clip and the functional part, illustrating other effects of the circular truncated conical engagement portions 24.

FIG. 6 is a partially enlarged plan view of the surgical clip 2 and the functional part 11, illustrating other effects of the circular truncated conical engagement portions 24.

Because each engagement portion 24 is rotatable within the associated hole 11a, the surgical clip 2 is rotatable on the tip of the arm 1 through the associated grip 22. The surgical clip 2 is maintainable at a predetermined rotation angle position with a frictional force between the functional part 11 and each circular truncated conical engagement portion 24, which results from a gripping force exerted by the functional part 11 on the arm 1.

Although not illustrated in detail, each engagement portion 24, for example, may be formed into a polygonal pyramid, or the outer periphery of each engagement portion 24 may be provided with gear-like protrusions and indentations and the inner surface of each hole 11b may be provided with projections that come into engagement with the protrusions and indentations. This enables rotation angle positioning of each grip 22 like a ratchet mechanism.

Enabling the surgical clip 2 to rotate relative to the arm 1 as described above makes it possible to place the surgical clip 2 at an optimal position where the surgical clip 2 will not reduce the visibility of an affected area during surgery.

Other Embodiments

As illustrated in FIGS. 1(a)-1(d), the circular truncated conical engagement portions 24 are provided with grooves 24a. In this embodiment, each groove 24a includes two grooves intersecting at a right angle and thus has a cross shape. One of the grooves of each groove 24a is formed to extend in a direction identical to an axis L of the surgical clip 2.

Bringing a stopper (not illustrated), which is provided on the functional part 11 of the arm 1, into engagement with the associated groove 24a restricts rotation of the surgical clip 2 relative to the arm 1. In this embodiment, the surgical clip 2 is rotated rightward or leftward by 90° such that the surgical clip 2 is fixable at the rotation angle position relative to the arm 1.

Figure 7:
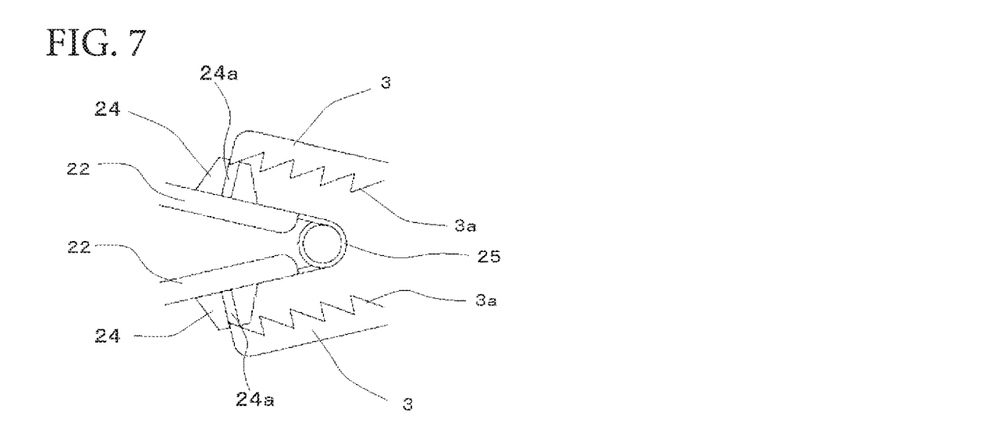

FIG. 7 is a partially enlarged plan view of the surgical clip 2 and the functional part 11, illustrating other effects of the grooves 24a.

Allowing the grooves 24a to come into engagement with teeth 3a on a tip 3 of an applier (which is, for example, another medical device) enables the surgical clip 2 to be gripped by the applier and brought into and out of an affected area. Allowing the surgical clip 2 to be gripped by another medical device (such as an applier) in this manner enables use of the surgical clip 2 for various types of procedures.

Figure 8:
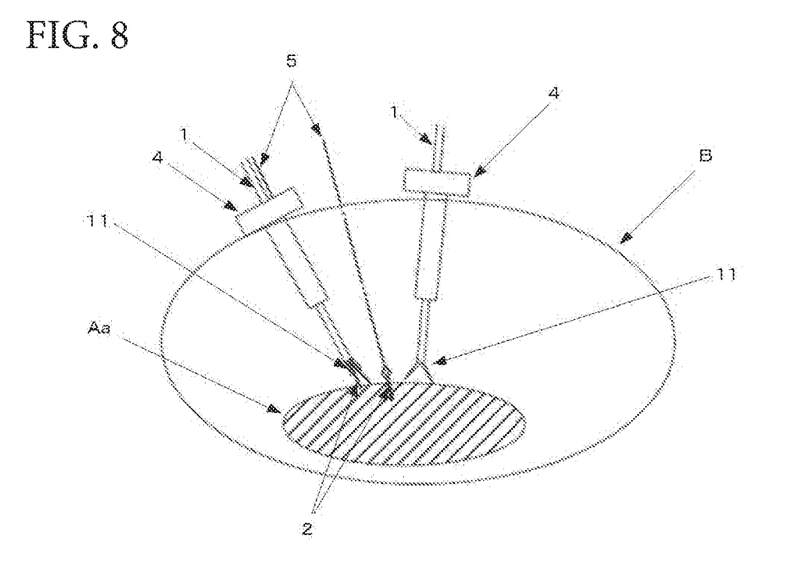
FIG. 8 is a diagram describing the effects of the surgical clip 2 according to the present invention and schematically illustrating an example of a procedure that involves using the surgical clip 2.
Figures 9A, 9B, 9C:
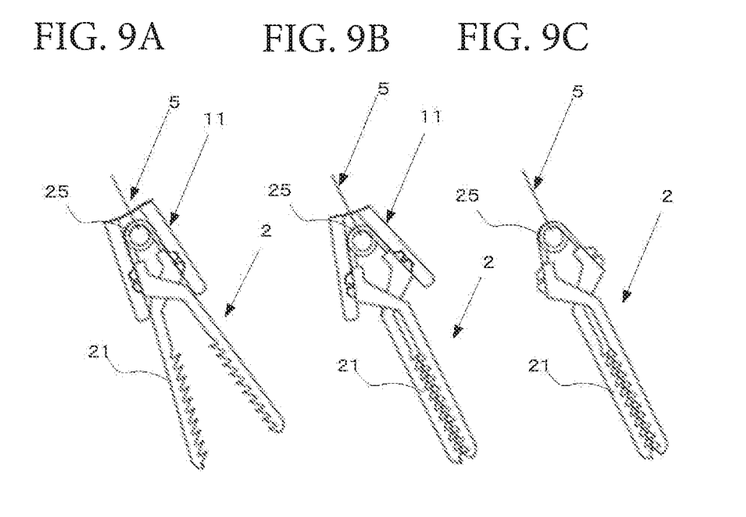
FIG. 9(a) is a diagram showing a condition where the holders are opened.
FIG. 9(b) is a diagram showing a condition where the holders are closed.
FIG. 9(c) is a diagram showing a condition where the functional part is removed from a surgical clip.

FIGS. 8 and 9(a)-9(c) are diagrams illustrating effects of the surgical clip 2 according to the present invention. FIG. 8 is a schematic diagram illustrating an example of a procedure that involves using the surgical clip 2. FIGS. 9(a)-9(c) are diagrams illustrating how the surgical clip 2 is operated.

A plurality of trocars 4 is inserted into a patient's body B. The surgical robot arms 1 whose functional parts 11 are gripping the surgical clips 2 are inserted through the trocars 4 and brought toward an affected area Aa. To perform this process, the springs 25 of the surgical clips 2 are connected with traction fibers 5 in advance. The surgical clips 2 are inserted through the trocars 4 and brought toward the affected area Aa together with the traction fibers 5.

Each functional part 11 is then operated in the closing direction, so that the holders 21 of the associated surgical clip 2 are opened. In this state (i.e., in the state illustrated in FIG. 9(a)), each arm 1 is operated so as to move the associated surgical clip 2 to a predetermined portion of the affected area Aa. Subsequently, each functional part 11 is operated in an opening direction, so that the holders 21 of the associated surgical clip 2 are closed. In this state (i.e., in the state illustrated in FIG. 9(b)), the predetermined portion of the affected area Aa is held by the surgical clips 2. After the predetermined portion of the affected area Aa is held, each functional part 11 is moved away from the associated surgical clip 2. In this state (i.e., in the state illustrated in FIG. 9(c)), the traction fibers 5 are dropped inside the patient's body B. Then, a traction instrument (which is to be used to remove the traction fibers 5 out of the patient's body B and whose diameter is as small as that of an injection needle) is inserted into the patient's body B. The traction fibers 5 are picked up and pulled out of the patient's body B by the traction instrument so as to apply traction to each surgical clip 2, thus pulling the affected area Aa.

If dedicated arms are necessary for each of surgical robots manufactured by different manufacturers or in accordance with different specifications, the surgical clip 2 according to the present invention would be gripped by the tip of any of the arms and would be able to perform an operation, such as holding the organ or other tissue. Thus, if a surgical robot has, for example, only three arms, the organ or other tissue would be held from a plurality of directions whose number exceeds the number of arms. This makes it unnecessary to install another surgical robot and requires only installing a small size robot including a minimum necessary number of arms. Consequently, the surgical clip 2 is able to provide a sufficient work area for, for example, a doctor or a nurse around an operating table.

The surgical clip 2 is able to prevent a disadvantageous situation where a large number of arms are in the way to block the practitioner's view or become obstacles during procedure. The surgical clip 2 is also able to avoid a disadvantageous situation where a single trocar is exclusively occupied by an arm for holding and pulling an organ or other body tissue.

The surgical clip 2 is usable in common for different affected areas, such as a stomach, a heart, a bladder, and a brain. The surgical clip 2 is more inexpensive than the dedicated arm 1 and enables efficient use of the arm 1. Accordingly, the surgical clip 2 is able to considerably reduce the cost of an operation that involves the use of a surgical robot.

Although the preferred embodiments of the present invention have been described thus far, the present invention is not limited to the above description.

In the above description, the surgical clip 2 serving mainly as a retractor, for example, has been illustrated by way of example. The surgical clip 2 having a similar structure, however, is also usable as forceps or a hemostatic clip.

The surgical robot arm, which is a medical device to grip the surgical clip according to the present invention, has been illustrated by way of example. The surgical clip according to the present invention, however, may be gripped by any other medical devices, such as forceps and appliers. As long as the surgical clip according to the present invention is capable of being gripped by such medical devices, the engagement portions 24 may be provided with projections and/or protrusions and indentations instead of or in addition to the grooves 24a.

Although the helical spring 25 has been illustrated as an example of an urger, any type of spring other than a helical spring or any urger other than a spring may be used as long as similar effects are achievable.

INDUSTRIAL APPLICABILITY

The present invention is applicable to a wide range of surgery involving the use of a surgical robot. The present invention is applicable not only to human surgery but also to animal surgery. Instead of forceps, the surgical clip according to the present invention may be used as an instrument to lift an organ or other body tissue.

REFERENCE SIGNS LIST 1 arm of medical device (surgical robot)
11 functional part
11a tooth
11b hole
2 surgical clip
21 holder
21a surface
22 grip
22a surface
23 tooth row
23a tooth
24 engagement portion
24a groove
25 spring (urger)
26 elongated hole
3 applier
3a tooth
4 trocar
5 traction fiber
Aa affected area (organ or other tissue)
B patient's body
S plane
L axis of surgical clip

The invention claimed is:

1. A surgical clip configured to be held by a functional part of a medical device, for pulling an organ or other body tissue so as to provide an area necessary for an operation, the surgical clip comprising:
   a pair of upper and lower holders configured to hold the organ or other body tissue therebetween;
   grip portions, each being connected to each of the upper and lower holders to open and close the upper and lower holders;
   an urger attached to the grip portions to constantly urge the upper and lower holders in a holding direction; and
   engagement portions, each being provided on an outer side of each of the grip portions and having a size configured to enter a hole of the functional part,
   wherein each of the engagement portions has a cone or polygonal shape projection including a frustum, with a tapered outer surface configured to engage the hole of the functional part, and
   each of the engagement portions is provided with an engagement groove configured to engage with a tooth or a projection provided on the functional part of the medical device.

2. The surgical clip according to claim 1, wherein each of the engagement portions is provided with a plurality of the engagement grooves at different angles.

3. The surgical clip according to claim 2 wherein the engagement grooves have a cross shape where two of the plurality of the engagement grooves cross each other.

4. A surgical clip configured to be held by a functional part of a medical device, for pulling an organ or other body tissue so as to provide an area necessary for an operation, the surgical clip comprising:
   a pair of upper and lower holders configured to hold the organ or other body tissue therebetween;
   grip portions, each being connected to each of the upper and lower holders to open and close the upper and lower holders;
   an urger attached to the grip portions to constantly urge the upper and lower holders in a holding direction; and
   engagement portions, each being provided on an outer side of each of the grip portions and having a size configured to enter a hole of the functional part,
   wherein each of the engagement portions has a cone or polygonal shape projection including a frustum, with a tapered outer surface configured to engage the hole of the functional part, and wherein the upper and lower holders include tooth rows facing each other, each including teeth configured to bite into the organ or other body tissue, the teeth are inclined toward a direction identical to a pulling direction, and the tooth rows on the upper and lower holders are deviated from each other such that the teeth are in mesh with each other in a staggered manner.

5. A surgical clip configured to be held by a functional part of a medical device, for pulling an organ or other body tissue so as to provide an area necessary for an operation, the surgical clip comprising:

a pair of upper and lower holders configured to hold the organ or other body tissue therebetween;

grip portions, each being connected to each of the upper and lower holders to open and close the upper and lower holders;

an urger attached to the grip portions to constantly urge the upper and lower holders in a holding direction; and engagement portions, each being provided on an outer side of each of the grip portions and having a size configured to enter a hole of the functional part, wherein each of the engagement portions has a cone or polygonal shape projection including a frustum, with a tapered outer surface configured to engage the hole of the functional part, and wherein each of the upper and lower holders has a rectangular shape with an elongated hole therein, and tooth rows arranged parallel to each other in a longitudinal direction thereof and spaced apart from each other with the elongated hole therebetween, the tooth rows of the lower holder engaging the tooth rows of the upper holder.

* * * * *